United States Patent [19]

Staats, III et al.

[11] Patent Number: 5,193,703

[45] Date of Patent: Mar. 16, 1993

[54] METHODS AND APPARATUS FOR FORMING AN INTEGRAL HIGH PRESSURE SEAL USING MECHANICAL ACTUATION

[75] Inventors: Louis T. Staats, III, Lincoln University, Pa.; James A. Bristow, Elkton, Md.; Anil P. F. Noronha, West Chester, Pa.; Gregory E. Murphy, Erial, N.J.

[73] Assignee: Hewlett-Packard Company, Palo Alto, Calif.

[21] Appl. No.: 825,450

[22] Filed: Jan. 22, 1992

Related U.S. Application Data

[63] Continuation of Ser. No. 487,655, Mar. 2, 1990, abandoned.

[51] Int. Cl.$^5$ .............................................. B65D 51/16
[52] U.S. Cl. .................................. 220/203; 220/234; 220/240
[58] Field of Search ........ 220/203, 204, 234, 235–237, 220/240, 370, 371, 303

[56] References Cited

U.S. PATENT DOCUMENTS

| | | | |
|---|---|---|---|
| 2,424,449 | 7/1947 | Gasche | 220/237 |
| 2,451,599 | 10/1948 | Wiltse | 220/240 |
| 2,492,225 | 12/1949 | Kester | 220/203 |
| 2,784,865 | 3/1957 | Rieke | 220/303 |
| 2,855,003 | 10/1958 | Thaxton | 220/237 |
| 3,203,576 | 8/1965 | Wout et al. | 220/304 |
| 3,289,878 | 12/1966 | Davenport | 220/203 |
| 3,490,488 | 1/1970 | Grist | 220/203 |
| 3,522,900 | 8/1970 | Nicholson | 220/203 |
| 3,923,192 | 12/1975 | Walters | 220/235 |
| 4,081,102 | 3/1978 | Sakai | 220/203 |
| 4,136,796 | 1/1979 | Dubois et al. | 220/303 |
| 4,142,648 | 3/1979 | Johnson et al. | 220/203 |
| 4,202,463 | 5/1980 | Mogler | 220/240 |
| 4,283,280 | 8/1981 | Brownlee | 210/198.2 |
| 4,313,828 | 2/1982 | Brownlee | 210/198.2 |
| 4,337,873 | 7/1982 | Johnson | 220/204 |
| 4,406,742 | 9/1983 | Dick | 196/14.52 |
| 4,440,308 | 4/1984 | Baker | 220/204 |
| 4,451,363 | 5/1984 | Brownlee et al. | 210/198.2 |
| 4,451,364 | 5/1984 | Higgins et al. | 210/198.2 |
| 4,457,846 | 7/1984 | Munk | 210/656 |
| 4,478,715 | 10/1984 | Goodnight, Jr. | 210/198.2 |
| 4,512,899 | 4/1985 | Goodnight, Jr. | 210/656 |
| 4,549,668 | 10/1985 | Krauss et al. | 220/203 |
| 4,666,056 | 5/1987 | Kasugai et al. | 220/203 |
| 4,696,409 | 9/1987 | Vize | 220/203 |
| 4,930,657 | 6/1990 | Walker | 220/235 |

*Primary Examiner*—Joseph Man-Fu Moy
*Attorney, Agent, or Firm*—Richard F. Schuette

[57] ABSTRACT

A cap for sealing pressure vessels is disclosed. The present invention permits a nominal closure to be formed by hand tightening and a substantially higher force to be applied to a cap by a separate clamp mechanism, thereby forming a pressure seal. In certain preferred embodiments, means for providing a process flow through a hole in the seal and filtering means are also provided as part of the cap assembly. A preferred application of the cap of the present invention is for the sealing of sample vessels used for supercritical fluid extraction of compounds from a solid matrix for subsequent chemical analysis. Methods of supercritical fluid extraction are also disclosed. The present invention thus provides methods and apparatus whereby the placement of a sample into a pressurized system may be automated and monitored to ensure adequate seals have been created and maintained within such pressurized systems.

25 Claims, 4 Drawing Sheets

METHODS AND APPARATUS FOR FORMING AN INTEGRAL HIGH PRESSURE SEAL USING MECHANICAL ACTUATION

CROSS REFERENCE TO RELATED APPLICATION

This is a continuation of copending application Ser. No. 07/487,655 filed on Mar. 2, 1990, now abandoned.

The present invention relates to methods and apparatus for sealing pressurized vessels. More particularly, the present invention relates to end-cap assemblies which may be initially installed by hand and subsequently actuated to provide a pressure seal for use in, for example, supercritical fluid extraction, and methods of achieving and maintaining such a seal.

BACKGROUND OF THE INVENTION

Frequently, there is a need within a variety of process applications to provide a seal for a pressurized vessel. Such a seal must contain the pressurized fluid without leaking. In the case of a threaded connection this requirement dictates that the mechanical engagement connecting the seal to the pressurized vessel be tightened with a substantial amount of force, thus the torque applied to the connection must be relatively high in order to provide a fluid-tight seal within the threads themselves or to create a force which acts upon a seal. This is an undesirable situation, however, since reliance is placed upon an operator to sufficiently tighten the seal to the proper torque without overtightening, which may damage the components.

Thus, in an instrument in which a pressurized fluid (typically supercritical or near-critical fluids, gases or liquids) flows through a vessel containing a sample (solid, semi-solids, small quantities of liquids) it is currently necessary to install sample containment vessels which require manual tightening of end caps using wrenches to seal the vessel. A second step of incorporating the sealed containment vessel within the system also requires making connections to the rest of the components using tubing fittings which also must maintain a high pressure seal. Additionally, some systems immerse the vessel in a thermal zone—e.g., ovens, heater blocks. As pointed out above, wrench-tightening to achieve seals is awkward and imprecise, and can be unreliable; this applies to cap seals as well as to connector seals. Nor is wrench-tightening amenable to automation; immersion in thermal zones can require many manipulations in addition to making all sealing connections, e.g., opening and closing oven doors, manipulating latch mechanisms, and affixing heater blocks. Implementation of the thermal zone within a pressurized system utilizing a sample containment vessel can therefore be a barrier to automation.

It would therefore be desirable to assume responsibility for creating high pressure seals within an extraction instrument to assure reliability and safety. Further, it would also be desirable to automate the sealing process. In many systems it is also desirable to provide improved access, e.g., "z-axis" (vertical) entry for interfacing with robotic systems or future autosampling systems implemented for the instrument. In many systems requiring the insertion and removal of a pressurized sample containment vessel it is further desirable to provide a thermal zone which would foster, not inhibit, automation. The sample containment hardware provided would preferably be analogus to typical laboratory supplies (overall geometry and volume, hand-tightened caps) and allows automatic tracking of the sample by incorporating details allowing labeling or machine readable coding, such as bar coding. A complete seal formation system would also provide means for the detection of leaks from any of the seal areas when the chamber is closed, and would provide safety interlock protection from the high forces required to produce an automated sealing process.

It is also desirable to provide a pressurized portion within a process which permits pressurized fluid to flow through a region while a seal is maintained. However, this facet adds a greater degree of complexity to formation of a seal when conventional threaded seals are used. For example, in certain chemical analytical sample preparation apparatus, the fluids being contained must be in the supercritical fluid phase. This requirement dictates that the sample be subjected to the appropriate conditions of pressure and temperature which result in the supercritical fluid state. Due to the serial nature of sample preparation with quantitative chemical analysis, a reliable seal is required. Also, due to the usual repetitiveness with which such chemical analyses are performed, a reusable high pressure seal is required. It would thus be desirable in the operation of such systems to provide a more reliable, long-life seal mechanism and a system which would verify sealing and provide diagnostic information (e.g., presence of all the input hardware). Also, since analysis is usually performed to ascertain certain characteristics of the sample, it is important that at least a nominal seal be maintained to prevent sample contamination or loss, and thereby retain sample integrity during all phases of sample preparation or analysis.

SUMMARY OF THE INVENTION

It is therefore a object of the present invention to provide methods and apparatus for forming a seal which may be easily installed to form a nominal seal, but which accurately and repeatedly forms a seal between the sealing apparatus and the pressurized vessel. It is a further object of the present invention to provide a seal which also permits pressurized fluid to flow through the pressurized vessel, such as the sample vessel used in supercritical fluid extraction.

A cap or similar sealing apparatus made in accordance with the present invention comprises a body portion which has threads o other appropriate detail adapted to engage the vessel which is being sealed. Within and movable relative to the body portion, sealing material is provided which can move and be compressed by the vessel after the threads have engaged the vessel. Preferably, the sealing material can slide relative to the body portion. In order to facilitate sliding or other movement, it is preferred that the sealing material be contained in a seal housing which is slidably movable with the sealing material relative to the body. Most preferably, the sealing material will be a substantially resilient material which will deform in a controlled manner to create a seal thereby permitting reuse. Also, in order to better facilitate movement between the body portion and the seal housing provided in certain embodiments, it is preferred that the seal housing be formed of a rigid material.

By including an opening in the body exposing the seal housing, an external force Can be applied to the seal housing for compressing the sealing material against the sealing surfaces of the vessel. Thus, a pressurized seal may be formed without increasing the torque and the resulting stresses in the threads of the cap. In applications requiring flow to or from the vessel, certain embodiments of the present invention may be provided with one or more openings running through the cap assembly while not interfering with the above-described relative motion between the components. In certain embodiments, a filter may be disposed across the opening in the cap assembly to prevent particulate contaminants from entering or leaving the sealed vessel.

The apparatus of the present invention is useful for practicing a method of applying a cap for sealing a vessel. Accordingly, it has now been found that a cap comprising a threaded portion and sealing which allows an operator to assemble the cap to a pressure vessel having a threaded portion to form a nominal closure thereby preventing loss or contamination of the vessel contents can be provided. Accordingly, the cap is applied to the vessel and the threaded portions are engaged. A high pressure seal can be subsequently formed by applying a force to the sealing material by or, in certain embodiments, to the seal housing by means of a separate clamping mechanism such as a pneumatic, hydraulic or electromechanical clamp. The sealing material is thus forced into sealing engagement with a sealing surface of the vessel after the body portion and vessel threads are engaged.

The cap of the present invention, when assembled to a pressure vessel, utilizes a threaded outer body to apply a load directly to the seal housing. This distributes a load over the seal and forces the seal against a seating surface on the pressure vessel. A nominal closure of the vessel is thus formed. In a preferred embodiment, the cap and vessel assembly leaves a face of the seal housing exposed to allow a clamping mechanism to fully load the seal housing. The design permits relative motion between the threaded outer body portion and the seal housing. This motion permits the seal to deform and prevents the clamp force from being transmitted to the outer body and damaging the threads.

The present invention also provides embodiments of a cap which comprise a through hole to allow a tapered tube, through which a pressurized process fluid can flow, to be inserted and forced against the seal material to form a second seal. Thus, an assembly of a cylindrical pressure vessel having a cap with a through-hole on both ends can be sealed by a single clamping action and provide a means to continuously flow through a vessel while maintaining a high pressure seal.

As will be understood by those of ordinary skill, for some applications a filter element such as a porous screen or other filter means can be assembled into the cap seal to filter the fluid stream flowing through the cap. The development of this feature for a particular application will require identification of the appropriate seal geometry to retain the filter element throughout a cycle of compression a decompression and resulting seal deformation.

A preferred application of the methods and apparatus of the present invention is the formation of a seal for use in a supercritical fluid extractor. A pressurized container for the extraction of compounds from a solid matrix is sealed using a cap made in accordance with the present invention. Thus, a sample vessel can be nominally sealed at one end, a sample loaded, and another end of the vessel nominally sealed using the caps provided herein. A pressure seal can then be formed by applying a compressive force to the caps. The extraction is then preferably performed by pumping solvent through the vessel via the caps. In a preferred embodiment, the force applied to the sealing material is sensed or, more preferably, continuously monitored to determine the sufficiency with which the container is sealed.

BRIEF DESCRIPTIONS OF THE DRAWINGS

DETAILED DESCRIPTION OF THE PREFERRED EMBODIMENTS

Figure 1:
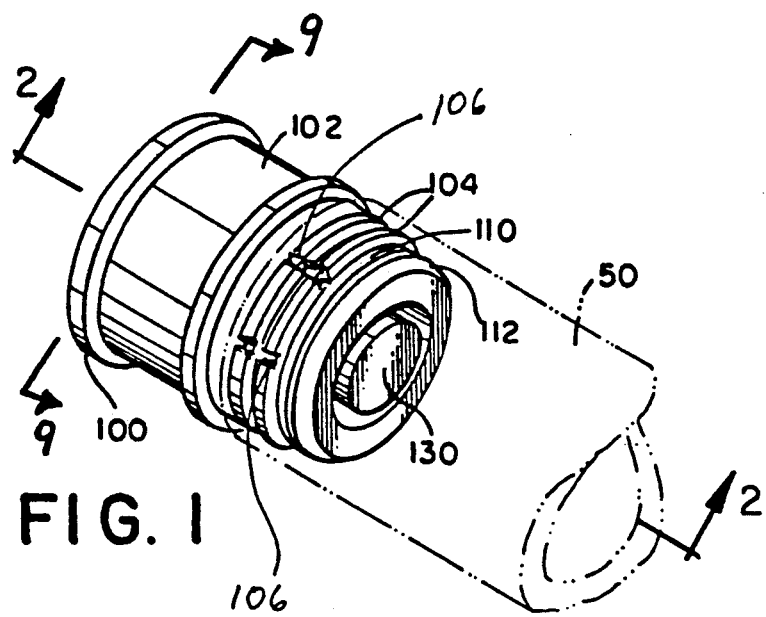
FIG. 1 is a perspective view of a preferred embodiment of a cap for forming a seal constructed in accordance with the present invention.

A perspective view of a preferred embodiment of a cap assembly 100 made in accordance with the present invention is shown in FIG. 1. An body portion 102 which engages a portion of the vessel to be sealed is provided with threads 104. In the context of the present invention threads or threaded connections will encompass a variety of mechanical detail which may be formed upon the mating portions of the cap and the vessel. For example, threaded connections are meant to include quarter turn fasteners and quick release fittings, such as those incorporating detent springs and the like. Numerous other fittings, such as swaged connections can also be readily adapted by those of ordinary skill for use in the present invention. Within the body portion 102, sealing material 112 is provided and disposed so as to be movable relative to the body portion 102, preferably in a slidable manner. The sealing material 112 is arranged to permit it to contact sealing surfaces within the vessel. In a preferred embodiment a seal housing 110 is provided to facilitate sliding movement between the body portion 102 and the sealing material 112.

Figure 2:
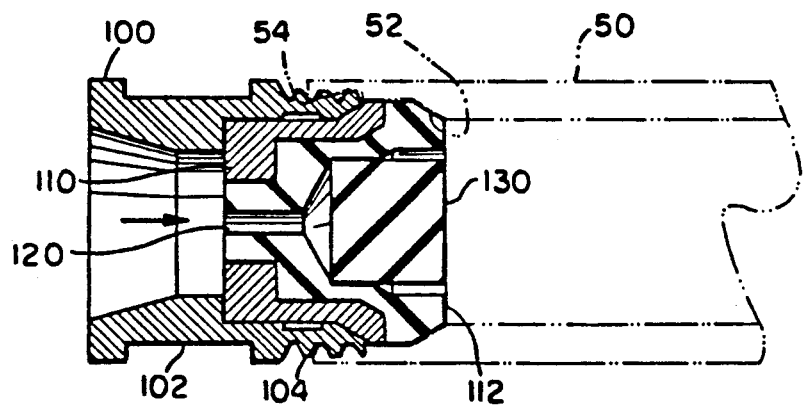
FIG. 2 is a cross-sectional view, taken along line 2—2, of a preferred embodiment of a cap for forming a seal constructed in accordance with the present invention which is installed in a vessel.

Referring now to FIG. 2 there is shown a cross-sectional view of a pressure vessel 50 having a reusable cap assembly 100 made in accordance with the present invention installed thereon. The pressure vessel 50 has a sealing surface 52 adapted for receiving a seal, and internal threads 54 for engaging the reusable cap assembly 100 itself is comprised of a body portion 102 and preferably has external threads 104 formed on a portion thereof. The threads 104 are constructed to engage the internal threads 54 in the pressure vessel 50. In certain embodiments it will be preferable to include pressure relief grooves 106 (shown in FIG. 1). These grooves permit excess pressure to be vented in the event the primary seal fails. Thus, the present invention permits an operator to hand assemble the cap 100 to a pressure vessel 50 to form a nominal closure which prevents loss or contamination of its contents.

Disposed within the outer body portion 102 of a preferred embodiment of the cap assembly 100 is a seal housing 110 which is loosely fitted and retained into the outer body portion 102. Disposed within and affixed to the seal housing 110 is the seal 112. As shown in FIG. 1 the seal 112 is shaped so as to engage the sealing surface 52 formed within the pressure vessel 50. As will be understood by those of ordinary skill, the seal 112 is preferably comprised of deformable material. Numerous materials suitable for the construction of the seal 112 are known and will be chosen based upon the particular application, for instance the material chosen should be relatively inert and impervious to the contained substances. Appropriate sealing materials include polyetheretherketone (PEEK TM), polytetrafluoroethylene (Teflon TM), elastomers, polymers, metals and a variety of plastic materials. As shown, the seal 112 conforms to the shape of the seal housing 110 and any force applied to the seal housing 110 is transferred to the seal 112.

Upon assembly, the threaded outer body portion 102 applies a load directly to the seal housing 110 which forces the sealing material 112 against the seating surface 52 on the pressure vessel 50. A nominal closure of the vessel 50 is formed when the threads 104,54 are engaged and tightened by hand or by a robot.

However, the assembly of the cap 100 of the present invention and the vessel 50 leaves exposed a face of the seal housing 110 which allows a clamping mechanism to load the seal housing 110 directly, as shown by the arrow in FIG. 2. In certain embodiments where the seal housing 110 is omitted, a porion of the seal 112 is exposed and accessible to a clamping force. This relative motion between the components is required so the force applied by the clamp does not result in force being transmitted to the body portion 102 which could damage the threads 104,54, but instead results in the further deformation of the sealing material.

As shown in FIG. 2, a concentric through hole 120 may be provided which will allow a tapered tube or other apparatus (not shown) to be inserted and forced through and against the seal 112. By forcing a tube into the hole 120, a second seal is formed at the interface of the tube and the sealing material through which a pressurized process fluid can flow without leakage. An assembly of a cylindrical pressure vessel 50 having a cap 100 made in accordance with the present invention with a through hole 120 attached to one or more locations can thus be sealed by a single clamping action and provide a means to continuously flow a fluid through the vessel 50 while maintaining pressure.

Additionally, for some applications it will be desirable to incorporate a filter element 130 as shown in FIG. 1. The filter element 130 is preferably comprised of a screen or porous frit which is assembled into the cap seal 112. As shown, the filter element 130 is most preferably held by surface interaction, such as a press fit. The geometry of the seal 112, and the seal housing 110 and the filter element 130 are chosen to retain the filter element 130 in its proper position throughout a cycle of compression and decompression, including the deformation of the sealing material 112 under a clamping force.

Figure 3:
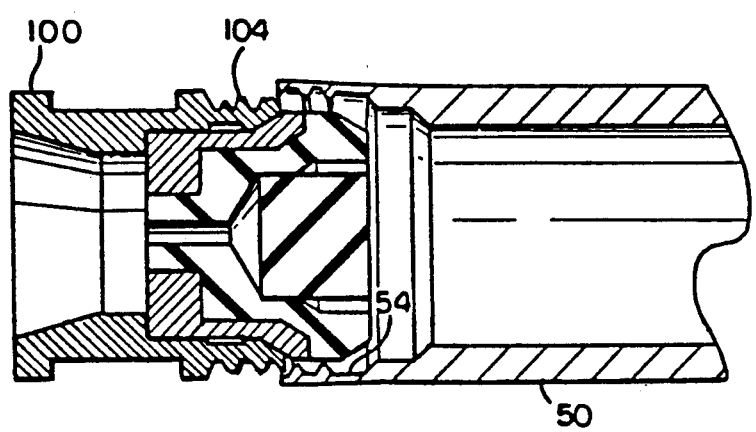
FIG. 3 is a cross-sectional view of the cap of FIG. 2, shown just prior to installation in a pressure vessel.
Figure 4:
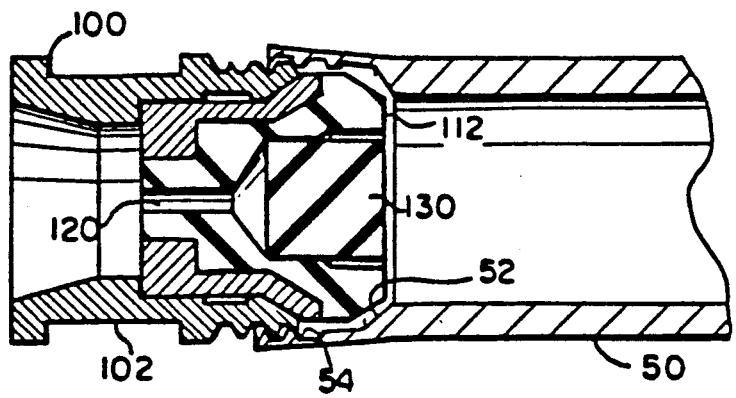
FIG. 4 is a cross-sectional view of the cap of FIG. 2 in the initial stage of installation, showing the threads engaged.
Figure 5:
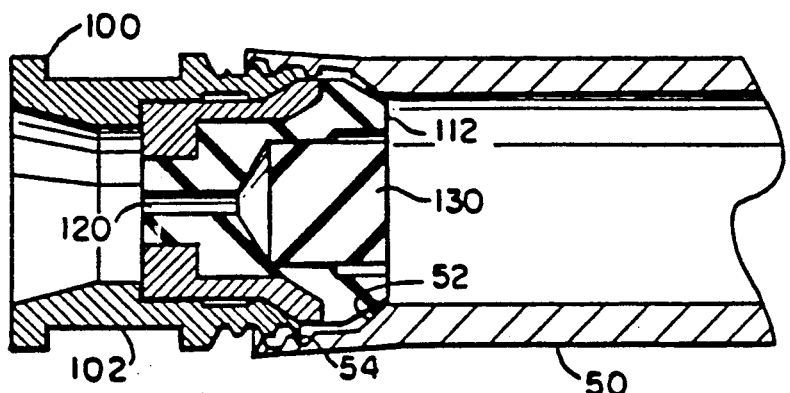
FIG. 5 is a cross-sectional view of the cap of FIG. 2, shown in the nominal seal position.

The sequence of installation using a preferred embodiment of the present invention is depicted in FIGS. 3-6. These figures show a cap 100 and vessel 50 substantially in accordance with that depicted in FIG. 2. As seen in FIG. 3, the cap 100 and vessel 50 are initially brought into engagement and the external threads 104 and the internal threads 54 are engaged. The body portion 102 of the cap 100 may then be manipulated to further engage the threads, as shown in FIG. 4. As the cap 100 is rotated, the sealing material 112 is moved closer to the sealing surface 52. The rotation continues until the sealing material 112 contacts the sealing surface 52 and forms a nominal seal, as shown in FIG. 5. It is understood that the installation of the cap 100 to this point has been preferably accomplished using hand tightening; therefore no significant torque or axial force has been applied to the cap 100 or the vessel 50 which will result in the plastic deformation of the seal or the threads 54,104.

Figure 6:
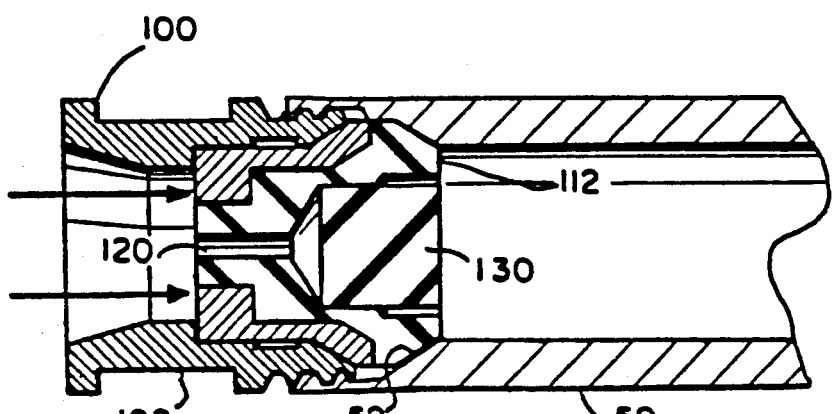
FIG. 6 is a cross-sectional view of the cap of FIG. 2 being urged by a clamping force into the fully sealed position.

To create a pressure seal which will maintain the contents of the vessel when a pressure is created therein, an external force is applied, preferably as shown in FIG. 6. As explained above, the construction of the cap 100 permits the sealing material 112 to move relative to the outer body 102. As shown, the sea 112 is urged against the sealing surface 52 and deformed. For this reason, the seal 112, or the housing 110 surrounding it, will most probably be displaced from the body portion 102 as shown.

The present invention provides a cap assembly which may be repetitively used to form a high pressure seal while maintaining a nominal seal when not under the influence of a clamping force, the nominal seal capable of being formed by hand tightening for ease of use and to prevent excessive stresses within the seal and the vessel. As pointed out above, the cap 100 of the present invention can be constructed using a portion of sealing material which functions as the seal housing 110, as well as the sealing material 112. In other words, the seal housing 110 as depicted is omitted and the sealing material 112 directly contacts the body portion 102. Thus, the pressure or absence of the housing 110 does not affect the functioning of the seal, but facilitates the sliding movement and the retention of the filter 130 depicted when provided in a preferred embodiment.

Figure 7:
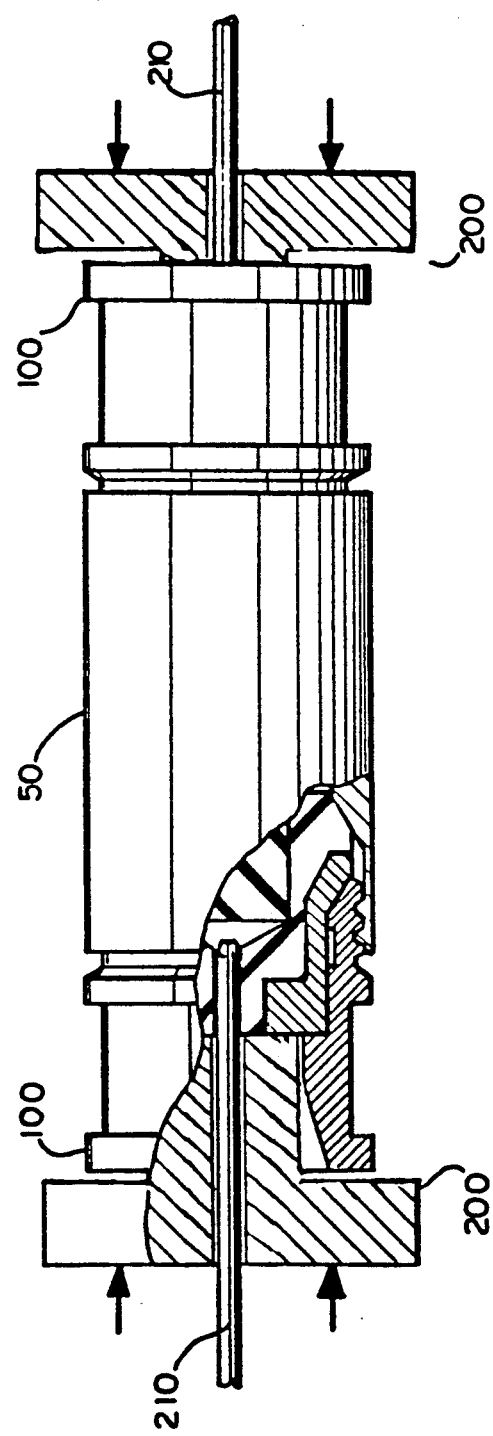
FIG. 7 is a partially broken away side view of a preferred embodiment of a cap for forming a seal, constructed in accordance with the present invention, installed at either end of a sample vessel.

A side view of a pressure vessel 50 for a pressurized flow process sealed using two caps 100 made in accordance with the present invention is shown in FIG. 7. A portion of the vessel 50 and one cap 100 have been broken away to permit the components of the sealed apparatus to be viewed. A specific application of the present invention is as a closure and seal for a sample container used for supercritical fluid extraction of compounds from a solid matrix. In this application, one end of a cylindrical sample vessel 50 is manually closed using a hand-tightened cap 100 with a filter 130 and through-hole 120 substantially as shown in FIG. 1. A solid sample is loaded through a second, open end of the vessel 50. After the sample has been loaded, the vessel is closed by hand tightening cap 100 on the second vessel end. Thus, the sample is now contained within the closed vessel and is protected from loss or contamination while awaiting extraction by the nominal seal formed by the two caps 100 each preferably made in accordance with the present invention. Prior to extraction, the vessel is placed into a clamping actuator (not shown) where clamping hardware 200 is brought into contact with the exposed end of the seal 110, and a compressive force, as shown by the arrows, is applied to create a high-pressure seal at each end. A tapered tube 210 is then inserted into each seal 100 by forcing the tube 210 through the through hole 120. By appropriately choosing the taper angle and outer diameter of the tube 210 relative to the diameter of the through hole 120, a force-fit seal which is maintained against the internal pressure of the vessel will be achieved. Extraction solvent is then pumped through the vessel at system pressure via the tubes 210 to perform the extraction; after extraction is complete, the system is depressurized and the clamp is opened. The vessel can now be removed with the remaining solid residue contained inside by the nominal seals. The residue may be processed further in the same vessel or may be discarded. When the sample is to be discarded, the caps can be removed by hand from both ends of the vessel to facilitate cleaning of the vessel and the caps.

In addition to the caps 100 used to form an integral high pressure seal discussed above, the present invention comprehends an apparatus for inserting a removable vessel within a pressurized fluid flow path, while automatically making high pressure seals and providing a controlled thermal environment. FIG. 7 depicts a preferred embodiment of a sealed vessel as well as the clamping hardware necessary to apply a compressive force to the assembly. When disposed within an instrument such as a supercritical fluid extractor or chromatograph, the portion of the instrument 250 where the sample resides will be constructed generally in accordance with FIG. 8. Preferably, apparatus made in accordance with the present invention will comprise a vessel 50 which is removable and which carries appropriate sealing surfaces, referred to as the cylindrical container. The cylindrical container 50 is typically disposed within a second vessel incorporating an actuator 225. The portion of the instrument in which the sealed vessel resides is referred to as the chamber body 250 and is mounted to the actuator by mounting plates 220 through which ball screws 230 are preferably threaded.

Thermal control components are sometimes incorporated within the chamber body 250. Since the force actuation produces relative movement, flexible cabling for thermal control components to accommodate the travel of the thermal zone is incorporated into certain embodiments. Similarly, flexible tubing coupling to the rest of the fluid system to accommodate the travel of the chamber body is also provided, as will be understood by those of ordinary skill. For example, each of the pin tubes 210 may be comprised of one or more flexible sections.

The apparatus of the present invention also preferably includes clamping hardware 200 which acts in concert with support assemblies integral with the frame of the chamber body 250 to apply the appropriate support and force to the sealing surfaces of each cylindrical container Cap 100. One container cap 100 is mounted against the stationary wall; the other assembly 225 is mounted to the chamber body 250 at the opposite end and moves during travel. Force sensing hardware & supporting electronics to apply required sealing force are incorporated into the chamber body/container cap interface. Actuation means such as ball screws 230 coupled to a worm gear train 232 are also provided. In a preferred embodiment two worm gear trains are driven synchronously by a stepper motor 234. Worm gear trains are preferred because the actuator will not back drive, thereby providing a fail-safe feature. The motor 234 which actuates the apparatus is preferably equipped with an encoder for diagnostics and control. Sensors provided at the closed and open positions of the actuator to verify position/movement and which can be used in concert with the motor encoder for diagnostics and control are also included.

The actuator 220 is contained within a housing 250 which interacts with the actuator and its movement to isolate the mechanism from interference through the access door 252 by sensing that the door has been closed and providing mechanical means 254 for preventing the door from opening at any time other than when a safe position has been achieved. Another safety feature is provided by the interaction of the actuator with the instrument covers so that the actuator cannot move when outer covers are removed. A final safety feature is the placement of a compliant ring 256 between the chamber halves which forms a low pressure seal when the chamber is closed. The ring 256 preferably has a tube attached to allow gas, which may escape during a leak condition, to be directed to a flow, or pressure transducer for purpose of leak detection.

Among the advantages the present invention provides is an increased reliability of high-pressure seals, because the force applied to the seal is not operator-dependent and can be controlled via the clamping mechanism to insure sufficient sealing stresses. Increased longevity of high-pressure seals is due to the operator-independent sealing force preventing excessive stresses being formed in a seal, which would decrease its useful life. The present invention also permits the formation of a nominal seal by hand closing seals made from materials with properties such that the stress required to form a gas tight seal would normally be higher than that which can be achieved in a typical hand tightened fitting. As will be appreciated by those of ordinary skill, this last advantage is significant, since it expands the range of useful sealing materials.

Methods for placing a vessel within a pressurized fluid stream region and making pressure seals safely and reliably are also disclosed. The methods of the present invention insure safe operation for the user during interaction and also include thermally controlling the apparatus. A process is initiated by capping one end of the removable cylindrical container through which the process fluid flows and placing the contents to be immersed in the fluid stream (the sample) within the cylindrical container, and then capping its other end. The operator (human or automation) places the cylindrical container within the thermally controlled region. Preferably, the cap is provided with a tapered section 58 as shown in FIG. 2. This taper guides the clamp 200 and the pin tube 210 into the central section of the cap, thereby aligning these components. Automatic centering of the cylindrical container is achieved so that the pin tubes mate with the pin tube seal Within the cap and the cylindrical container cap seal is aligned with the clamping hardware which will exert the cap sealing force.

Figure 8:
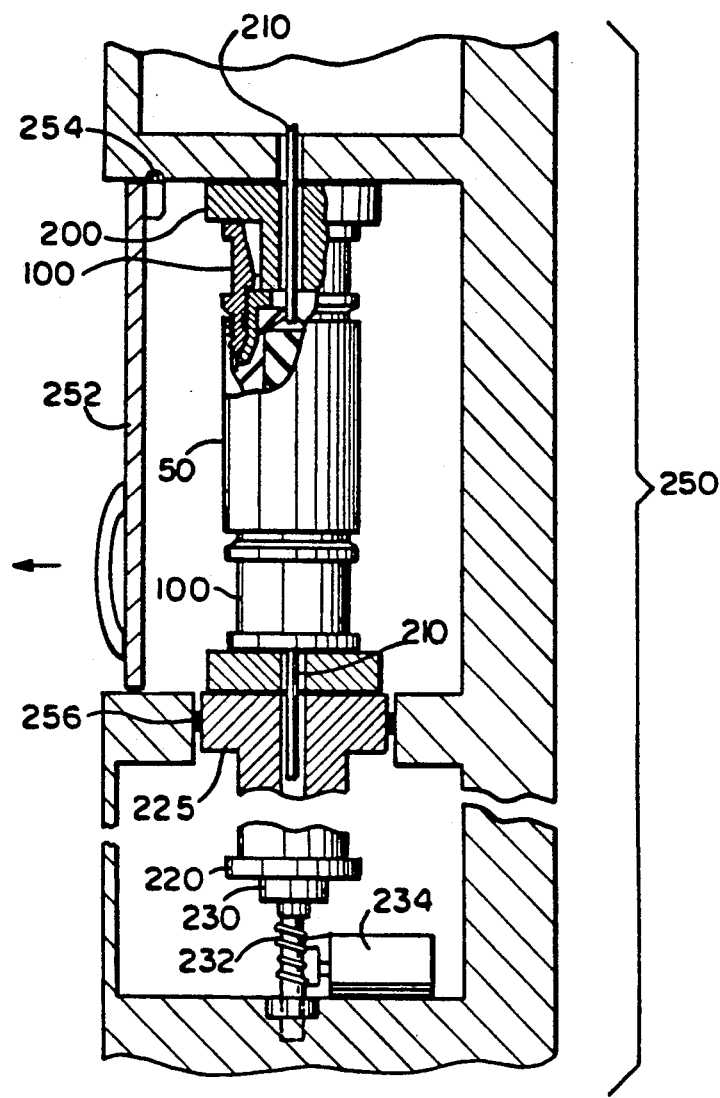
FIG. 8 is a partially broken away cross-sectional side view of an instrument made in accordance with the present invention having a vessel sealed as shown in FIG. 7.
Figure 9:
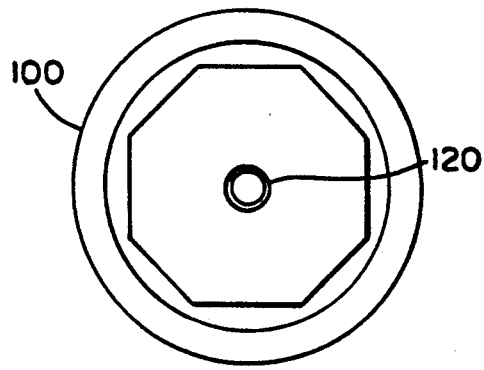
FIG. 9 is an end view of the cap of the present invention, as shown by the arrows 9—9 in FIG. 1.

Referring to FIG. 8 the vessel, caps and other hardware described above are preferably contained in a housing having a safety door with a closure sensor and latch. Worm gears 232 or other actuation devices are provided which cause the chamber to move create high pressure seals by forcing the end caps into the sealing position. The instrument is given a "Start" command and the safety door closure is sensed; a control system actuates the motor to move the worm gears 232. If the door is closed it is mechanically latched in place and the position of the door is sensed thereafter. If the door is open, actuation is interrupted or most preferably reversed and position of the apparatus restored to a safe state.

As explained above, the caps of the present invention facilitate the alignment of the clamping hardware and pin tubes, this permits the chamber to engage the pin tube so that contact is made between the pin tube and the mating sealing surface on the cap, and so that the clamping hardware contacts the appropriate annular area on the thimble cap. The caps are then loaded to a predetermined load by the actuation drive. The system continues to drive the cylindrical container within the chamber, i.e., increases the compressive force; urging the caps against the sample container until either the motor stalls at a predetermined torque limit, or a force sensor indicates that appropriate sealing forces have been achieved and the motor is subsequently stopped.

Preferably, if the required torque or sealing force is not achieved or a sensor determines that a sample container is not present, a warning or diagnostic routine is initiated. The system of the present invention may use, for example, an encoder to determine the displacement the apparatus undergoes and also initiate a warning or diagnostic routine if the displacement is not within the mechanical tolerance limits for making a seal.

At this stage in the method of the present invention, if no diagnostic or warning routines have been initiated, the actual process programmed into the instrument can be initiated since an adequate seal has been formed. After the instrument has completed the process, sensors determine whether the conditions for opening chamber are satisfied. If appropriate conditions of temperature and pressure exist, the motor is actuated to open the chamber. However, if the temperature and pressure exceed allowable limits, a cooling and pressure relief system is activated to reduce the temperature within the chamber thermal zone to a defined value.

Conditions being satisfied, the drive opens the chamber. Hardware is provided so that as the chamber begins to open, the pin tubes are pulled out of engagement with the caps. As the chamber opens, this hardware continues to move, displacing the sample container partially out of the chamber body, for easy access for removal. The chamber travels to its original open position, casing the latch to be released, thereby allowing the safety door to be opened. A sensor determines the location of the apparatus to detect when the mechanism is fully opened and mechanical stops are provided, should the open position sensor circuit fail. During the entire cycle, whenever the apparatus of the present invention is in motion or under pressure, the presence of the instrument cover is sensed to ensure that it is in place at initiation and remains there, protecting the user from the moving apparatus or in case of system failure, such as uncontrolled venting.

As will be realized by those of ordinary skill, there are an number of implementations for controlling the seal force. For example, a torque limited motor can be driven to stall at a torque limit (an open loop implementation). The torque applied is known; the friction and torque loss created by the geometry of the drive components the can be accounted for. Therefore, torque losses or variations in drive efficiency can be compensated for.

Alternatively, a system can be constructed to sense via a force transducer the actual applied force and turn the motor off when the appropriate force is achieved (a closed loop). The latter closed loop is the preferred embodiment. Once sealing of the cylindrical container within the system is achieved, the extraction process or other method can proceed. In a typical extraction process, the cylindrical container is filled with fluid to a given pressure and flow is established such that the pressurized fluid enters one end of the cylindrical container, and sweeps through the volume and out the other end. Upon completion of the programmed extraction process, sensors are checked to determine that conditions for opening chamber are satisfied (i.e., pressure, temp, door closed), the seal formation process is essentially reversed. The drive opens the chamber, as the chamber begins to open, the pin tubes are pulled out of engagement with the caps by strippers or other apparatus for withdrawing the pin tubes, which are required to keep the caps from sticking to self-locking taper of pin tube seal surface. As the chamber continues to open, one stripper continues to move displacing the cylindrical container partially out of the chamber body for easy access for removal. The chamber travels to its original open position causing a latch to be released to allow the safety door to be opened for access to the cylindrical container. Both electronic sensing and mechanical stops are used at the bottom of travel to assure proper travel (i.e., to avoid over travelling) and feedback to the controlling software or other sensing circuitry that opening has been achieved.

Certain embodiments of the method of the present invention also include means for controlling the temperature of the cylindrical container containing the sample according to specifications appropriate for the useful exploitation of supercritical fluid properties. The design of the chamber held by the mounting plates provides appropriate thermal breaks, heat exchange device and sensor mounting, and insulation. Thermal performance of the instrument's chamber body (particularly for response time, stability, and uniformity) may be optimized by the appropriate choice of material and design geometry. For faster cycle time of this large-mass thermal zone, a thermal pull-down may preferably be incorporated; this feature not only improves cycle time but also is a safety feature because the cylindrical container is cooled before the user removes it from the chamber thermal zone.

Another safety feature which may be included in certain embodiments of the present invention is the incorporation of a sensor to determine that the outer cover which overlays the sample input module cover is in place so that when the internal part of the instrument is accessed for maintenance and/or trouble-shooting, automatic movement of the actuator carriage is disallowed.

The present invention also provides closed loop force control for mechanically actuated seals such as those described above. Methods for achieving containment of fluids within a specified, detachable and removable region, defined by a container or other vessel, by an automated sealing system using an actuator device coupled with electronic feedback are provided as set forth below. Preferably, force control is achieved by a method comprising the steps of placing the container in an actuator device which undergoes relative movement and causes all the sealing components to be placed in contact with each other and then placed under a compressive force. The methods of the present invention then monitor the force created using a transducer (e.g., a force or pressure transducer), and issues a signal indicative of the magnitude of force or, in certain embodiments, a simple status signal. The signal generated is of a first value when the appropriate force between contacting components is achieved and is therefore indicative of normal operating conditions. The method of the present invention also uses the transducer-originated signal for monitoring the status of the force between sealing components after appropriate sealing forces have been attained to maintain the seal. Preferably, a method performed in accordance with the present invention uses any change in the form or magnitude of the electronic signal originating at the transducer to control the subsequent movement of the mechanical actuator. In other words, a quantitative signal can be generated to control the force precisely should it change during any point in the process being monitored. Alternatively, the signal could be a simpler "GO/NO GO" step function-type signal which caused the actuator force to be increased until a threshold limit was reached, causing additional force to be applied if the container "relaxed." The latter type of control is less precise and cannot reduce the actuation force unless an upper force limit is also monitored, which would require additional logic in the monitor circuit, as understood by those of ordinary skill. Thus, the use of the transducer-originated signal in conjunction with logic and possibly other types of sensors can alert the user that the appropriate sealing force has not been achieved when those cases arise.

The cylindrical pressure vessel or "thimble" is preferably sealed at both ends with a bevel seal/seat arrangement, as shown in FIG. 7. The cylindrical container may contain pressures on the order 10,000 psi when used, for example, in a supercritical fluid extraction instrument. The force required to create a seal is dependent on the seal/seat geometry, the seal material, the pressure, and the medium contained. The force feedback system of the present invention allows precise control of the load applied to the seals and allows the nominal force setpoint to be electronically varied.

Among the advantages of the system disclosed is improved seal reliability. The present invention insures that a minimum force is applied to successfully seal a container without applying excessive loads which could damage the seal components. Seal force is independent of actuator efficiency, which varies with environmental conditions and actuator life. Furthermore, unit-to-unit actuator efficiency may vary enough that extreme precautions with respect to both individual actuator component specification and actuator assembly processes would be necessitated in order to achieve reliable sealing if the actuator were operating in an open-loop mode.

The system of the present invention increases seal component life in several ways. First, no excessive force is applied to the seal/container assembly. Second, the applied load can be adjusted to meet pressure requirements to match the force exerted on the seals to the force exerted by the pressure from within the container. Also, the applied load can be adjusted to be appropriate to different sealing materials or adjusted for wear in the seal itself.

The present invention also has a beneficial effect on the life of the actuators used to exert a compressive force on the seal and container assembly. Since no excessive loads have been placed on the actuator system, as explained above, less wear results. Secondly, the automatic compensation for changes in actuator efficiency increases the useful life of a given actuator and also extends the intervals between actuator maintenance. The present invention permits the use of multiple seal component materials in a standard actuator by providing a force limit which is electronically set and optimized for specific material properties. Finally, the system disclosed provides diagnostic information; if the required force is not achieved during seal actuation, a diagnostic message can be presented for corrective/preventative maintenance without losing sample integrity. Thus, by continuous monitoring of force on the transducer, a characteristic force versus time waveform can be detected, thereby indicating a leak in the system and allowing for immediate increase in applied load to stop the leak and/or provide a diagnostic message to the user. Further diagnostic information is provided by monitoring downstream flow or pressure, the seal can be re-tightened or increased force used to maintain a seal.

Those of ordinary skill will realize that the caps and pressure vessels disclosed herein are useful within numerous other systems. The present invention thus provides a multi-function, multi-use apparatus for retaining a sample and performing operations upon the sample in one or more instruments. The present invention, for example can be used in solid phase extraction from a liquid. In accordance with the present invention, a method of extracting components from a liquid matrix comprising the step of providing a sample vessel adapted to receive a seal and containing a granular packing material and forming a nominal seal on said sample vessel is contemplated. As set forth above, by applying a compressive force to said vessel a pressure seal is formed. A liquid sample is then flowed through said sample vessel and a component will preferably be adsorbed on to the granular filler. By pumping extraction fluid through said vessel to perform the extraction of components from said granular packing material, permitting the components to be dissolved from said packing material and collected in concentrated form. Such extractions may utilize a supercritical fluid.

The cap and vessel of the present invention also lend themselves to methods of filtering particulates from a fluid stream. A sample vessel adapted to receive a seal and to be transferred to an extraction instrument is preferably provided. Next, a nominal seal is formed on said sample vessel and a compressive force applied to said nominal seal to create a pressure seal. By directing said fluid stream into said sample vessel while forming a nominal seal at another end of said vessel using a cap having a filter element therein, filtration is accomplished.

Although certain embodiments of the present invention have been set forth with particularity, the present invention is not so limited. Accordingly, reference should be made to the appended claims in order to determine the scope of the invention.

What is claimed is:

1. A cap for sealing a vessel having a shoulder for engaging sealing material comprising:
   a body portion having a proximal end and a distal end, wherein the distal end extends into the vessel the body portion including details for engaging the vessel;
   a sealing body comprised of sealing material disposed substantially within said body portion, the sealing body comprising: a distal portion that tapers from a first diameter to a second, smaller diameter at a distal end; and a proximal portion that is selectively engaged with an external force that urges the distal portion of the sealing body into sealing engagement with the shoulder by sliding the sealing body relative to the outer body.

2. The cap of claim 1, wherein the distal end of the sealing body extends into the vessel a greater distance than the distal end of the body portion.

3. The cap of claim 1, further comprising a seal housing containing said sealing body, said seal housing disposed substantially said body portion and being slidably movable with said sealing body relative to said body portion.

4. The cap of claim 3, wherein said body portion includes an opening exposing a face of the seal housing at a proximal end of said seal housing so as to permit the external force to be applied to said seal housing for compressing said sealing body against said shoulder.

5. The cap of claim 3, wherein said body portion, said seal housing and said sealing body have one or more openings running therethrough so as to permit fluid to flow to or from said vessel.

6. The cap of claim 5 further comprising a filter means disposed across said opening.

7. The cap of claim 6 wherein said filter is retained in said cap by surface interaction provided by the geometry of said filter, said sealing body and said body portion.

8. The cap of claim 1, wherein said sealing material is formed of a deformable material.

9. The cap of claim 3, wherein said seal housing is formed of a rigid material.

10. The cap of claim 1 wherein said details comprise threads.

11. The cap of claim 1 wherein said details comprise a snap fastener.

12. The cap of claim 1 wherein said details comprise quick release connection.

13. The cap of claim 1, further comprising venting means for substantially limiting the stress in said details caused by the pressure released from said vessel.

14. The cap of claim 13, wherein said venting means comprise longitudinal slots.

15. The cap of claim 1, further comprising label means for identifying said vessel.

16. The cap of claim 4, wherein said opening is substantially hexagonal.

17. The cap of claim 4, wherein said opening is frusto-conically shaped.

18. Apparatus for sealing a pressurized vessel having tapered section for receiving a seal and means for receiving threads, the apparatus for sealing comprising:

(a) a body portion having a distal end and comprising threads; and
(b) seal means for mating with said tapered section for receiving a seal, wherein the seal means comprises a distal portion extending beyond the distal end of the body portion that tapers from a first diameter to a second, smaller diameter at a distal end, and a proximal portion that is selectively engaged with an external force, said seal means movable within said body portion, whereby the threads disposed on the body portion are engaged with the means for receiving threads of the vessel and tightened to form a nominal closure, and whereby the external force moves said seal means relative to said body portion and urges said seal means into the vessel and against the tapered section to form a pressurized seal.

19. The apparatus of claim 18, further comprising one or more axial bores through said body portion and said seal means.

20. The apparatus of claim 19 further comprising means for filtering a fluid disposed across at least one of said axial bores.

21. The apparatus of claim 18 further comprising a seal housing disposed between said sealing means and said body portion, and wherein said seal housing has a proximal end for receiving force.

22. A pressurized container for the extraction of components from a solid matrix comprising a pressure vessel, said pressure vessel having a removable cap for creating a high pressure seal, said cap comprising:

(a) an outer body portion comprising details for engaging the pressure vessel; and
(b) seal means for sealing said pressure vessel disposed substantially within said outer body portion and being movable relative to said outer body portion, the seal means further comprising a distal portion that tapers from a first diameter to a second, smaller diameter at a distal end, and a proximal portion that is selectively engaged with an external force, whereby the threaded portion engages the pressure vessel and creates a nominal seal, and the application of the external force to the seal means moves the seal means relative to the outer body portion and urges the seal means against the vessel to create a high pressure seal.

23. The pressurized container of claim 22 wherein said pressure vessel has at least two ends each sealed by a removable cap.

24. The pressurized container of claim 22, wherein said cap further comprises an axial bore disposed in said body portion and said seal means.

25. The pressurized container of claim 24, wherein said cap further comprises means for filtering a fluid disposed across said bore.

* * * * *